United States Patent
Porter et al.

(10) Patent No.: US 11,484,633 B1
(45) Date of Patent: Nov. 1, 2022

(54) MULTI-STAGE BLOOD WARMING SYSTEM THAT ENABLES FIELD DELIVERY OF HEATED BLOOD

(71) Applicant: ARCHEMEDIC SOLUTIONS, LLC, San Diego, CA (US)

(72) Inventors: Glen Stephen Porter, San Diego, CA (US); Harry Ryan, San Diego, CA (US)

(73) Assignee: ARCHEMEDIC SOLUTIONS, LLC, San Diego, CA (US)

( * ) Notice: Subject to any disclaimer, the term of this patent is extended or adjusted under 35 U.S.C. 154(b) by 0 days.

(21) Appl. No.: 17/714,105

(22) Filed: Apr. 5, 2022

(51) Int. Cl.
*A61M 1/02* (2006.01)
*A61M 1/36* (2006.01)

(52) U.S. Cl.
CPC ........ *A61M 1/0281* (2013.01); *A61M 1/0209* (2013.01); *A61M 1/369* (2013.01); *A61M 2205/3327* (2013.01); *A61M 2205/3331* (2013.01); *A61M 2205/3334* (2013.01); *A61M 2205/3368* (2013.01); *A61M 2205/368* (2013.01); *A61M 2205/3633* (2013.01);
(Continued)

(58) Field of Classification Search
CPC .. A61M 1/0209; A61M 1/0281; A61M 1/369; A61M 2205/3327; A61M 2205/3331; A61M 2205/3334; A61M 2205/3368; A61M 2205/3633; A61M 2205/3653; A61M 2205/368; A61M 2205/8206
See application file for complete search history.

(56) References Cited

U.S. PATENT DOCUMENTS

| | | | | |
|---|---|---|---|---|
| 4,808,159 A | * | 2/1989 | Wilson | A61M 5/445 604/113 |
| 7,020,388 B2 | * | 3/2006 | Mills | F21V 29/59 392/407 |

(Continued)

OTHER PUBLICATIONS

Weatherall, A, Gill M, Milligan J, et al.; Comparison of portable blood-warming devices under simulated and pre-hospital conditions: a randomized in-vitro blood circuit study. *Anaesthesia.* 2019 (74): 1026-1032.

(Continued)

*Primary Examiner* — Benjamin J Klein
(74) *Attorney, Agent, or Firm* — Arc IP Law, PC; Joseph J. Mayo (57) ABSTRACT

A multi-stage system for warming blood that enables safe and rapid blood transfusions in the field. The first stage of the system is a rapid blood warming device that heats blood quickly from cold storage to body temperature. This stage may use a high-energy power source, such as AC power, that is available in a facility such as a hospital. The second stage is a portable heated blood transport device into which heated blood bags are placed for transportation to a patient. This device keeps the blood bags warm using battery power. Because blood bags are pre-heated with the rapid warming device, the transport device can be lightweight and portable. An optional third stage is a transfusion temperature regulating device that boosts the final temperature of blood just before it enters the patient. All three devices may have sensors and controllers that maintain blood temperature within desired ranges.

15 Claims, 6 Drawing Sheets

(52) U.S. Cl.
CPC ............... *A61M 2205/3653* (2013.01); *A61M 2205/8206* (2013.01)

(56) References Cited

U.S. PATENT DOCUMENTS

| | | | |
|---|---|---|---|
| 7,236,694 B1* | 6/2007 | Chammas | A61M 5/44 604/113 |
| 2003/0216689 A1* | 11/2003 | Bouhuijs | A61M 5/44 604/113 |
| 2022/0143287 A1* | 5/2022 | Zarate | A61M 1/369 |

OTHER PUBLICATIONS

Martin MJ, Holcomb JB, Polk T, Hannon M, et al.; The "Top 10" research and development priorities for battlefield surgical care: Results from the Committee on Surgical Combat Casualty Care research gap analysis. *J Trauma Acute Care Surg*. Jul. 2019;87(1S Suppl 1): S14-S21.

Eastridge BJ, Mabry RL, Seguin P, et al.; Death on the battlefield (2001-2011): implications for the future of combat casualty care. *J Trauma Acute Care Surg*. Dec. 2012; 73(6 Suppl 5): S431-7.

Harvin, JA, Maxim, T, Inaba, K, et al. Mortality following emergent trauma laparotomy, Journal of Trauma and Acute Care Surgery: Sep. 2017—vol. 83—Issue 3—p. 464-468.

Lehavi A, Yitzhak A, Jarassy R, et al.; Comparison of the performance of battery-operated fluid warmers, *Emergency Medicine Journal*. Sep. 2018. 35(9): 564-570 (retrieved from https://www.ncbi.nlm.nih.gov/pmc/articles/PMC6109241/).

The Belmont Rapid Infuser, FMS2000 Operators Manual; 53 pages (retrieved on Mar. 31, 2022).

Jones TB, Moore VL, Shishido AA. Prehospital Whole Blood in SOF: Current Use and Future Directions. J Spec Oper Med. 2019 Winter; 19(4):88-90. PMID: 31910478.

Avstreih DB, Morgan JI, Evans C. Blood on Demand: Designing an EMS Massive Transfusion Program. *EMS World*. May 2019 (retrieved from https://www.emsworld.com/article/1222566/blood-demand-designing-ems-massive-transfusion-program).

* cited by examiner

MULTI-STAGE BLOOD WARMING SYSTEM THAT ENABLES FIELD DELIVERY OF HEATED BLOOD

BACKGROUND OF THE INVENTION

Field of the Invention

One or more embodiments of the invention are related to the field of medical devices and systems for blood transfusions. More particularly, but not by way of limitation, one or more embodiments of the invention enable a multi-stage blood warming system that enables field delivery of heated blood.

Description of the Related Art

In many emergency trauma cases, it is necessary to transfuse blood in the field rather than waiting until the patient can be transported to a hospital. Illustrative trauma situations requiring in-field transfusion may include military injuries, motor vehicle accidents, natural disasters, terrorist attacks, and gunshot injuries. Providing blood to an injured patient quickly may be essential to prevent loss of life. A major challenge in enabling rapid transfusions in the field is the need to warm blood to body temperature before transfusing, since transfusing cold blood into a patient would exacerbate the hypothermia that the patient is likely experiencing due to blood loss. This hypothermia could lead to death of the patient while also causing excruciating pain. Blood is generally stored and transported at near-freezing temperature (4° C.) for preservation, and it must then be warmed to be used in the field.

Resuscitation and hemorrhage management in trauma patients in pre-hospital settings are currently among the US military's top ten medical priorities (see "The 'Top 10' research and development priorities for battlefield surgical care: Results from the Committee on Surgical Combat Casualty Care research gap analysis", July 2019). This is exemplified in a report of all combat casualties in Iraq and Afghanistan, as 91% of preventable deaths were attributed to massive blood loss (see "Death on the battlefield (2001-2011): implications for the future of combat casualty care", December 2012). In the US, nearly 40% of civilian casualties are attributed to hypotension (low blood pressure associated with blood loss) due to hemorrhage, which has not changed in the past two decades (see "Mortality after emergent trauma laparotomy", September 2017). There is therefore a critical need in both military and civilian settings for an effective portable blood warming to treat victims of severe blood loss in the field.

While there are portable blood warming devices available on the market, researchers have shown that they do not meet the required temperature specifications for a successful blood transfusion. In a prospective randomized controlled bench-test study of four portable, battery-operated warming devices published in the May 2019 edition of Anaesthesia, the products tested did increase the blood temperature but did not reach normal body temperatures (37° C.) (see "Comparison of portable blood-warming devices under simulated and pre-hospital conditions: a randomized in-vitro blood circuit study", 2019; and "Comparison of the performance of battery-operated fluid warmers", September, 2018). Infusing blood into a patient at only a few degrees lower than body temperature will escalate the patient's hypothermia due to the rapid blood loss. The four products were evaluated for heating performance over time, measured as 1) volume that can be effectively heated and 2) flow resistance. The products tested were: Belmont Buddy Lite (Belmont Instrument Corporation, Billerica, Mass., USA), CareFusion enFlow (CareFusion Corporation, San Diego, Calif., USA, now Vyaire Medical, Mettawa, Ill., USA), Thermal Angel TA-200 (Estill Medical Technologies, Dallas, Tex., USA) and QinFlow Warrior (QinFlow, Tel-Aviv, Israel). The research findings concluded that all four fluid warmers failed to warm the blood to an acceptable body temperature of 37° C. from chilled conditions. Additionally, the four fluid warmers failed to warm the blood at a high flow rate even from a 10° C. input, when in field operations, blood is typically stored at an even lower refrigerated temperature of 4° C. The researchers concluded that the energy transfer from these devices is too inefficient for infield usage.

Although there are effective blood warming devices that will meet the required temperatures, such as the Belmont® Rapid Infuser FMS2000, these are not designed for portability or for use in the field. This device weighs 28 lbs. and requires 115-120 VAC or 230 VAC to operate. It does have a lead-acid battery for backup power. However, the fluid warming feature is disabled when transporting patients (see "The Belmont® Rapid Infuser, FMS2000 Operators Manual"). The currently available portable blood warming devices used in the military are ineffective and heavy to transport; as a result these blood warming devices are rarely carried out into the field (see "Prehospital Whole Blood in SOF: Current Use and Future Directions", Winter 2019). In the civilian setting, whole blood collection and transfusion kits are available in only 34% of paramedics in the US (see "Blood on Demand: Designing an EMS Massive Transfusion Program", May 2019), which often means that refrigerated blood cannot be warmed and transfused in-route to the nearest medical facility.

This critical gap in technology in the field of portable FDA-cleared blood warming medical devices to prevent infusion-based iatrogenic hypothermia for massive blood loss poses a serious dilemma for the medics and doctors arriving at the emergency scene to attend to the injured. Rapid and accurate blood replacement would increase the chances of survival in injured patients when transfusion does not exacerbate hypothermia, but this requires that blood be warmed quickly in the field. Current blood warming devices are either not portable and unsuited for use in the field, or portable but not sufficiently powerful to adequately warm blood in the field.

For at least the limitations described above there is a need for a multi-stage blood warming system that enables field delivery of heated blood.

BRIEF SUMMARY OF THE INVENTION

One or more embodiments of the invention may enable a multi-stage blood warming system that enables field delivery of heated blood. The system may combine multiple devices to provide a solution that delivers heated blood to patients in the field that can be transfused immediately upon delivery.

One or more embodiments of the invention may combine a first stage of a rapid blood heating device and a second stage of a portable heated blood transport device. The rapid blood heating device may have an input line that is configured to be coupled to a supply of unheated blood, a line coil coupled to the input line where blood is heated, and a heating device output line coupled to the line coil and configured to be connected to a blood bag and to supply heated blood into the blood bag. The rapid blood heating device may also contain a heating device heating element proximal to the line coil that is configured to heat blood passing through the coil; this heating element may be configured to be coupled electrically to a high-energy power source. The rapid blood heating device may also have a heating device output temperature sensor coupled to the heating device output line, which measures the temperature of blood passing through the heating device output line. The rapid blood heating device may also have a heating device controller coupled to the heating device output temperature sensor and to the heating device heating element, which is configured to adjust the heat output of the heating device heating element to maintain the temperature measured by the heating device output temperature sensor within a desired heating device temperature range. The portable heated blood transport device may have a case that is configured to open and close with an insulated cavity configured to receive one or more blood bags filled with heated blood. The portable heated blood transport device may also contain a battery within the case, a transport device heating element coupled to the battery and located proximal to the blood bags, a transport device storage temperature sensor located proximal to the blood bags, and a transport device controller. The controller may be coupled to the transport device heating element and to the transport device storage temperature sensor, and it may be configured to adjust the heat output of the transport device heating element to maintain the temperature measured by the transport device storage temperature sensor with a desired transport device temperature range.

In one or more embodiments of the invention the high-energy power source may include an alternating current power source.

In one or more embodiments of the invention the heating device heating element may include an infrared lamp.

In one or more embodiments of the invention the rapid blood heating device may also have a reflective material surrounding the line coil, which reflects wavelengths emitted by the infrared lamp. This reflective material may be aluminum for example.

In one or more embodiments of the invention the rapid blood heating device may also have a heating device input temperature sensor coupled to the input line and configured to measure the temperature of blood passing through the input line.

In one or more embodiments of the invention the rapid blood heating device may also have a bubble sensor that is configured to detect bubbles in blood passing through the heating device output line.

In one or more embodiments of the invention the rapid blood heating device may also have a heating device flow rate sensor that measures the flow rate of blood through the rapid blood heating device.

In one or more embodiments of the invention the portable heated blood transport device may also have a transport device output line, an inflatable bladder in the case that is in contact with the blood bags, and an air source coupled to the inflatable bladder and to the transport device controller. The transport device controller may be configured to inflate the inflatable bladder when the transport device controller receives a command to initiate a transfusion.

In one or more embodiments of the invention the transport device controller may also be configured to periodically inflate the inflatable bladder to mix blood within the blood bags during transport.

In one or more embodiments of the invention the portable heated blood transport device may also have a pressure sensor that measures the pressure of air in the inflatable bladder.

In one or more embodiments of the invention the portable heated blood transport device may also have a transport device output temperature sensor coupled to the transport device output line.

One or more embodiments of the invention may also include a third stage of a transfusion temperature regulating device. This regulating device may have a regulating device input line that is configured to receive blood from one or more blood bags in the portable heated transport device, a power line configured to be electrically coupled to the battery of the portable heated blood transport device, a line heating path coupled to the regulating device input line, a regulating device heating element coupled to the power line and proximal to the line heating path and configured to heat blood passing through the line heating path, a regulating device output line coupled to the line heating path and configured to be coupled to a transfusion line into a patient, a regulating device output temperature sensor coupled to the regulating device output line, a regulating device controller, and a communications interface configured to communicate with the transport device controller. The regulating device controller may be coupled to the regulating device output temperature sensor and to the regulating device heating element, and it may be configured to adjust the heat output of the regulating device heating element to maintain the temperature measured by the regulating device output temperature sensor within a desired regulating device temperature range.

In one or more embodiments of the invention the regulating device controller may also be configured to transmit a command to the transport device controller to modify the heat output of the transport device heating element based on the temperature measured by the regulating device output temperature sensor.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A multi-stage blood warming system that enables field delivery of heated blood will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
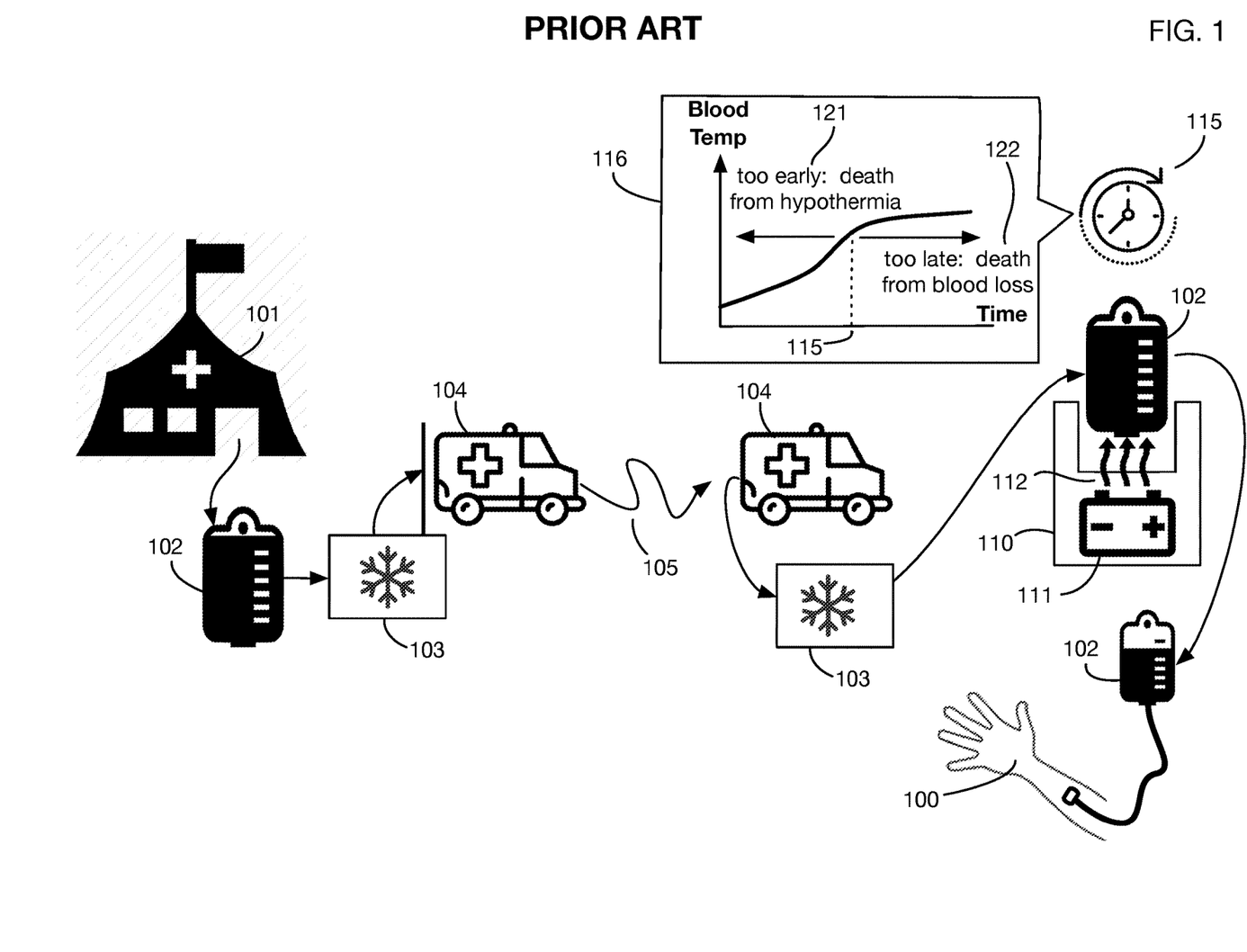
FIG. 1 shows an illustrative field blood warming system generally available in the prior art, which attempts to use a battery-powered device to heat blood from a cooled temperature; this type of system may not be effective at heating blood rapidly enough to enable a timely transfusion of heated blood for an injured patient.

FIG. 1 shows a typical approach used in the prior art to deliver blood to a patient 100 in the field. A facility 101, which may be a fixed hospital or a temporary field hospital for example, has a supply of stored blood. Patient 100, who is remote from the facility, needs an in-field transfusion. Facility 101 therefore provides one or more units of blood 102 that are transported to the patient's location. Transportation over distance 105 may be performed using a vehicle 104 or by a person, such as a military medic, travelling on foot and carrying the blood. In many situations the blood is transported in a cooled environment 103, such as a cooler, to prevent contamination or degradation of the blood during transport.

Ideally the blood 102 is then warmed prior to transfusion to prevent hypothermia in the patient 100. In some situations, a portable blood heating device 110 may be available to warm the blood 102 when it is removed from cold storage 103 upon delivery. This device, if present, is typically powered from a battery 111. A major challenge is that a battery that is small enough to be portable provides a relatively small flow of heat 112 to warm the blood 102. This presents a dilemma since the time 115 to heat the blood to the appropriate temperature (approximately 37° C.) may be very long using such a device. The graph 116 of blood temperature as a function of time indicates the dual risks of transfusing too early 121 when the blood is too cold, which risks death or injury from hypothermia, or waiting too long 122 until the blood is sufficiently warm, which risks death of the patient from blood loss while the blood is warming.

In some situations, a portable blood warmer 110 may not be available at all, which requires medical personnel to resort to ad hoc warming solutions such as using a warm water bath, which may be even less efficient. Even when a portable blood warmer 110 is available, it may not be sufficiently lightweight or compact to be transported on foot, for example, such as in a battlefield situation.

Figure 2:
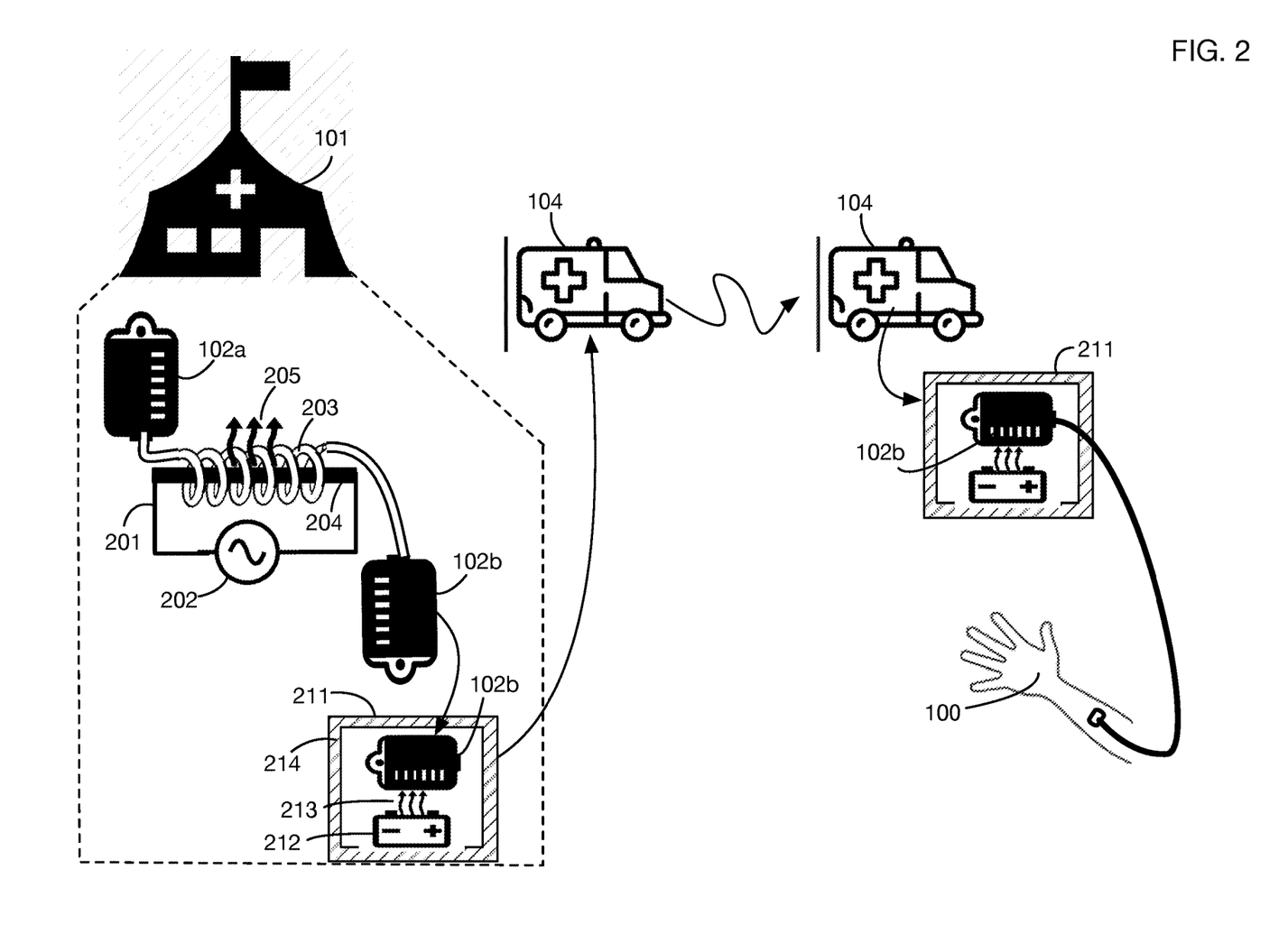
FIG. 2 shows an architectural diagram of an illustrative embodiment of the invention; this two-stage system includes a rapid blood heating device that may be used to heat blood prior to transport, and a portable heated blood transport device that maintains the heated blood at a an appropriate temperature so that transfusion can occur immediately when the blood reaches the patient location.

FIG. 2 shows an illustrative embodiment of the invention, which uses a different approach compared to the largely unsuccessful attempts in the prior art to heat blood at the point of transfusion. In the system shown in FIG. 2, blood from a blood bag 102a, which may be taken from cold storage, is first heated in facility 101 using a rapid blood heating device 201. Because this process occurs in the facility 101 rather than in the field, the facility has access to a high-energy power source 202, such as an AC power source or a high-capacity battery or generator. This high-energy power source enables rapid heating of blood 102a to the appropriate temperature for a transfusion. Because the device 201 heats blood very rapidly, the facility can store blood at a cold temperature and then heat blood on demand, for example when a notification arrives that blood is needed in the field. The rapid blood heating device 201 therefore enables a different paradigm of blood delivery to the field that heats blood prior to transport using a high-energy power source that need not be portable. An illustrative rapid blood heating device 201, which is described in greater detail below with respect to FIG. 3, passes blood through a coil 203 of tubing that surrounds an infrared lamp 204; the heat 205 emitted by the infrared lamp is rapidly and efficiently absorbed by the blood, enabling a high flow rate through the coil 203. The heated blood exits the coil 203 and enters another blood bag 102b that contains the heated blood.

A second element of the embodiment of the invention shown in FIG. 2 is a portable heated blood transport device 211. The heated blood bag 102b is placed into this device 211 for transport, for example in a vehicle 104 or in a backpack of a medic. This transport device 211 has a case with an insulated cavity 214 that contains the heated blood bag 102b; the insulation maintains the heated blood bag at or near its desired temperature during transport. In addition, to compensate for some heat loss through the insulation, the transport device 211 has a heating element powered by an internal battery 212 or a similar portable energy source. Because the blood in bag 102b has been pre-heated to the desired temperature before being placed into transport device 211, this battery 212 only needs to provide a relatively small amount of heat 213; as a result, the battery can be considerably smaller than batteries of existing purportedly portable blood heating units that are often not used because they are too heavy and impractical. Device 211 with the contained heated blood bag (or bags) 102b can therefore be lightweight and easily transported. In addition, the small heat flow 213 needed to maintain the temperature of blood bag 102b is provided throughout transport, rather than upon delivery to the patient's site, so there is no appreciable delay in getting blood to the desired temperature. As shown in FIG. 2, upon arrival at the patient site, blood can be transfused directly from device 211 into patient 100.

These two elements of the invention, the rapid blood heating device 201 and the portable heated blood transport device 211, therefore work together as a two-stage system to provide a heated blood delivery system that eliminates the dilemma illustrated in graph 116 of FIG. 1. Medical personnel need not choose between early delivery of cold blood or late delivery (if ever) of sufficiently heated blood, because the blood arrives in a heated state ready for use. The preheating of blood in facility 101 with a high-energy heating device 201 also allows transport device 211 to be small and truly portable. This two-stage system that combines a first stage of a rapid pre-heating device and a second stage of a truly portable transport device that provides heated blood immediately to a patient in the field is not known in the prior art.

Figure 3:
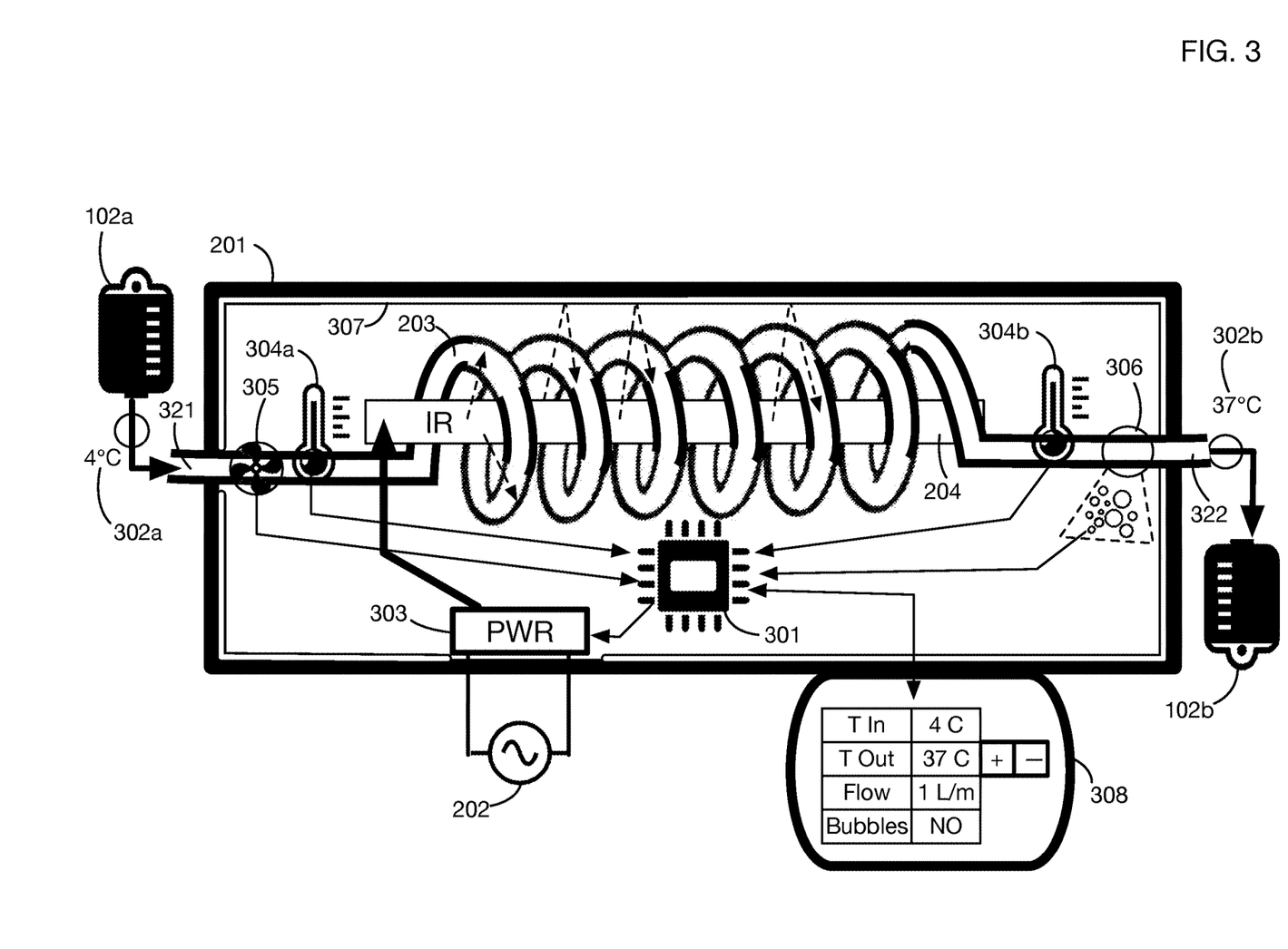
FIG. 3 shows illustrative components of an embodiment of the rapid blood heating device.

FIG. 3 shows illustrative components of an embodiment of a rapid blood heating device 201. The device includes a path for blood flow that includes an input line 321, a line coil 203 coupled to the input line, and an output line 322 coupled to the line coil. In one or more embodiments the input line 321, the line coil 203, and the output line 322 may be integrated into a contiguous path of tubing; they are not necessarily (although they may be) discrete elements. Input line 321 is attached to blood bag 102a (or another blood source) that contains unheated blood, which may be for example at a cold storage temperature 302a. Output line 322 is attached to output blood bag 102b that contains heated blood at temperature 302b. Line coil 203 wraps around heating element 204. The coil 203 may be of any shape; the helical coil shape shown in FIG. 3 is illustrative. Any path for blood that brings the path near the heating element 204 is within the spirit of the invention. In one or more embodiments the heating element 204 may wrap around the blood path, rather than the blood path wrapping around the heating element as shown in FIG. 3.

Heating element 204 may be for example an infrared (IR) lamp or similar element. An illustrative IR lamp that may be used in one or more embodiments is a Ushio 1350w Quartz Infrared Heater Halogen Lamp. In one or more embodiments coil 203 may be of a material that allows the infrared or other wavelengths emitted by heating element 204 to penetrate the coil and heat the blood. Illustrative coil materials may include for example glass Pyrex or polymers such as PFA.

Rapid blood heating device 201 may also have reflective surfaces 307 that surround all or a portion of coil 203; these surfaces may reflect wavelengths emitted from heating element 204 back into the device 201, to increase the efficiency of blood heating. Reflective surfaces 307 may be for example aluminum. The reflective material may be attached to the inner surface of an insulated housing surrounding the coil and the heating element.

Heating device 201 may include sensors and a control system to ensure that blood is heated to a temperature that is within a desired range and to monitor for any problems during the heating process. It may contain a heating device controller 301, which may be for example, without limitation, a microprocessor, a microcontroller, a processor, a CPU, a GPU, an ASIC, or a network connection to any other processor or processors. Data from sensors within the heating device 201 may be transmitted to the controller 301. Illustrative sensors may include for example an input temperature sensor 304a that measures the temperature of incoming blood, and output temperature sensor 304b that measures the temperature of outgoing blood, a flow sensor 305 that measures the flow rate of blood through the device, and a bubble sensor 306 that monitors the blood for bubbles. These sensors are illustrative; one or more embodiments of the rapid heating device may include any desired sensors.

Controller 301 may control a power modulation element 303 that sets the power level flowing from power source 202 to heating element 204. Power source 202 may be any source with sufficient power to drive the heating element 204 to achieve the desired rapid heating of the blood, including but not limited to an alternating current power source. Element 303 may use for example pulse-width modulation control to modify the power flowing to heating element 204. Any type of power modulation technique may be used in one or more embodiments of the invention. A feedback control loop may be implemented using controller 301 to modify the power transmitted to heating element 204 to achieve the desired output temperature 302b measured by output temperature sensor 304b. Controller 301 may for example use a PID control loop or any other feedback control technique to monitor temperature and adjust heating power accordingly to maintain the output temperature within a desired range.

In one or more embodiments of the invention, rapid heating device 201 may include a user interface display 308 that communicates with controller 301. This display may be for example a touchscreen integrated into or attached to the device, or it may be an external display coupled to the device via a network connection. The user interface may display data from the device sensors, and it may provide options for example to adjust the output temperature of the blood or to adjust any other controllable parameters such as flow rates.

The components shown in FIG. 3 for device 201 are illustrative; one or more embodiments may include a rapid heating device with any subset of these components or with any additional components.

Figure 4:
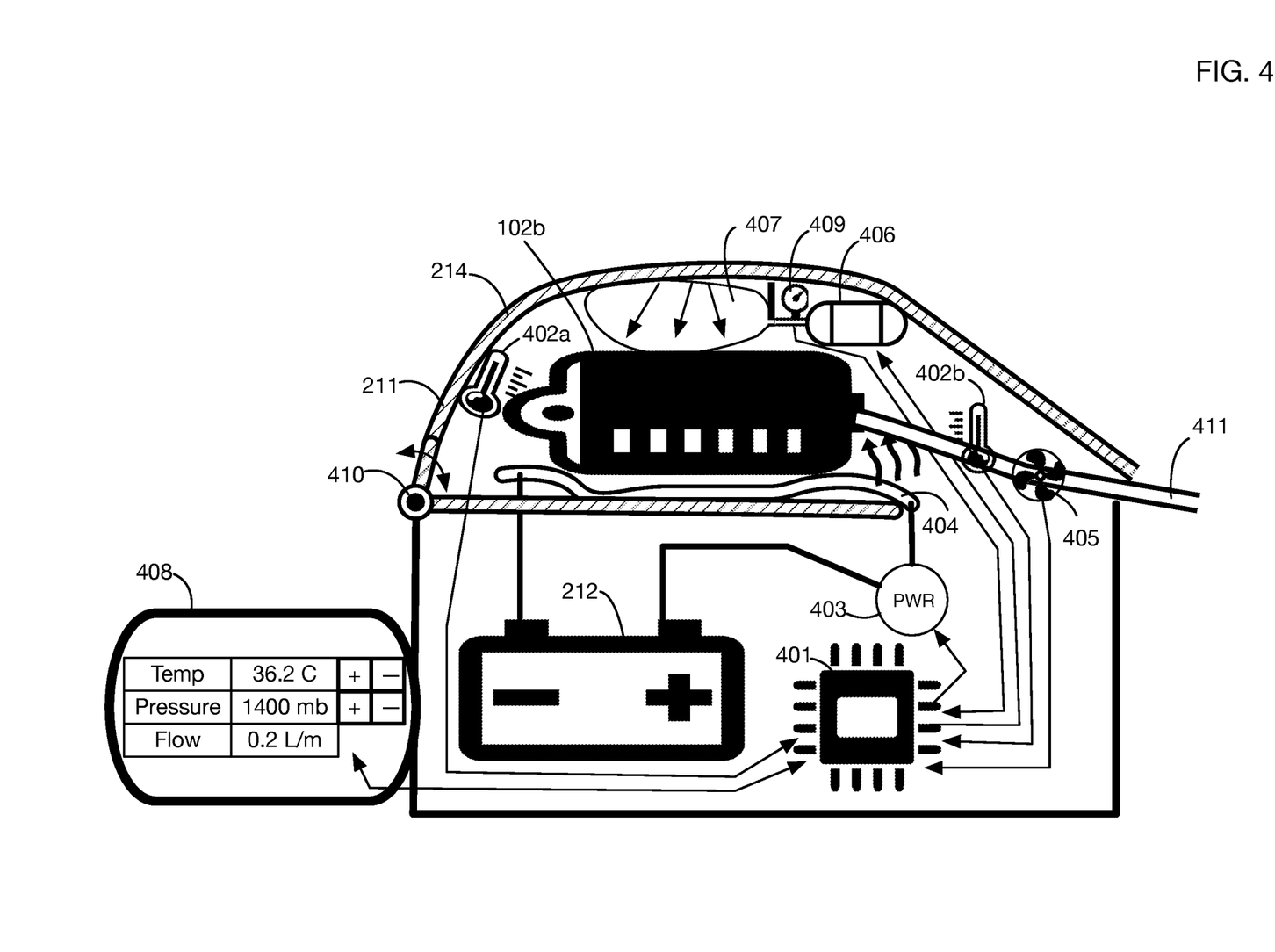
FIG. 4 shows illustrative components of an embodiment of the portable heated blood transport device.

FIG. 4 shows illustrative components of an embodiment of a portable heated blood transport device 211. This device may contain a case with an insulated cavity into which one or more heated blood bags 102b (which may have been heated by rapid blood heating device 201) may be placed for transport. A transport device 211 may have any desired capacity for the number of heated blood bags it can contain. An illustrative insulating material 214 that may be used in one or more embodiments is aerogel insulation. The transport device case may open and close in any desired manner; for example, the top cover may flip open around a hinge 410 to receive the heated blood bags. One or more heating elements 404 may be in contact with or proximal to the heated blood bags to provide additional heat during transport to maintain the bags within a desired temperature range. For example, in one or more embodiments the heating element(s) 404 may be flexible heating elements that may conform to the shape of the contained heated blood bags. Heating element(s) 404 may be powered by a battery 212 contained in the transport device 211. Battery or batteries 212 may be for example rechargeable lithium-ion batteries. One or more embodiments may power the heating elements using any desired power source, such as a battery of any type, a solar power system, or an energy harvesting system.

An output line 411 may be coupled to one or more of the heated blood bags 102b contained in the transport device 211. In one or more embodiments it may be possible to attach the output line 411 to a contained heated blood bag without opening the case of the transport device, so that blood may be transfused directly from the transport device without opening it, thereby minimizing potential heat loss. In one or more embodiments output lines for each contained blood bag may be integrated into the transport device and attached when the blood bags are placed into the device, and a transfusion line may be coupled to one or more exposed ports on the outside of the transport device case.

In one or more embodiments transport device 211 may include one or more components that apply pressure to the contained blood bag(s) to enable transfusion of blood directly from the contained bags into the patient in the field. This capability may eliminate the need to hang the blood bags for gravity fed transfusion, which may be impractical in many situations. For example, in a combat situation a medic may need to stay low for protection, so hanging a blood bag may be dangerous. In a space environment, gravity may be absent and applying pressure to the blood bag may be the only available method for transfusion. Applying pressure to a blood bag in the transport device also saves time since the bag need not be removed from the transport case. In the embodiment shown in FIG. 4, pressure is applied to blood bag 102b via an inflatable bladder 407 that is coupled to a source of air 406. The air source 406 may be for example a compressor or a cylinder of compressed air.

Transport device 211 may include a transport device controller 401 that controls the heating element 404 and the air source 406. Controller 401 may be for example, without limitation, a microprocessor, a microcontroller, a processor, a CPU, a GPU, an ASIC, or a network connection to any other processor or processors. Transport device 211 may also include sensors that provide data to controller 401. Illustrative sensors may include for example storage temperature sensor 402a that measures the temperature of the contained blood bag(s), output temperature sensor 402b that measures the temperature of outgoing blood, a flow sensor 405 that measures the flow rate of blood from the blood bag(s), and a pressure sensor 409 that measures the pressure of the inflatable bladder. These sensors are illustrative; one or more embodiments of the transport device may include any desired sensors.

Transport device controller 401 may control a power modulation element 403 that determines the power flowing from power source 212 to heating element 404. For example, element 403 may use pulse-width modulation control to modify the power flowing to heating element 404. Any type of power modulation technique may be used in one or more embodiments of the invention. A feedback control loop may be implemented using controller 401 to modify the power transmitted to heating element 404 to maintain the temperature of the enclosed blood bag(s) within a desired range, as measured for example by storage temperature sensor 402a, and to ensure that the output temperature of blood flowing from the blood bags, as measured by output temperature sensor 402b, is adequate for transfusion. Controller 401 may for example use a PID control loop or any other feedback control technique to monitor temperature and adjust heating power accordingly.

Transport device controller may also control the air source 406 to achieve a desired pressure, as measured by pressure sensor 409, or a desired output flow rate, as measured by output flow sensor 405. In one or more embodiments, the air source may be activated periodically during transport (prior to a transfusion) to mix the blood in the enclosed bag(s) 102b; mixing may help maintain uniform temperature of the blood within the bags and may help prevent coagulation.

In one or more embodiments of the invention, transport device 211 may include a user interface display 408 that communicates with controller 401. This display may be for example a touchscreen integrated into or attached to the device, or it may be an external display coupled to the device via a network connection. The user interface may display data from the device sensors, and it may provide options for example to adjust the output temperature of the blood or to adjust other controllable parameters such as flow rates or pressures. A user may enter commands into this user interface to initiate a transfusion for example, which may cause the controller 401 to start or adjust flow of air from the air source 406 into inflatable bladder 407.

The components shown in FIG. 4 for device 211 are illustrative; one or more embodiments may include a portable heated blood transport device with any subset of these components or with any additional components.

Figure 5:
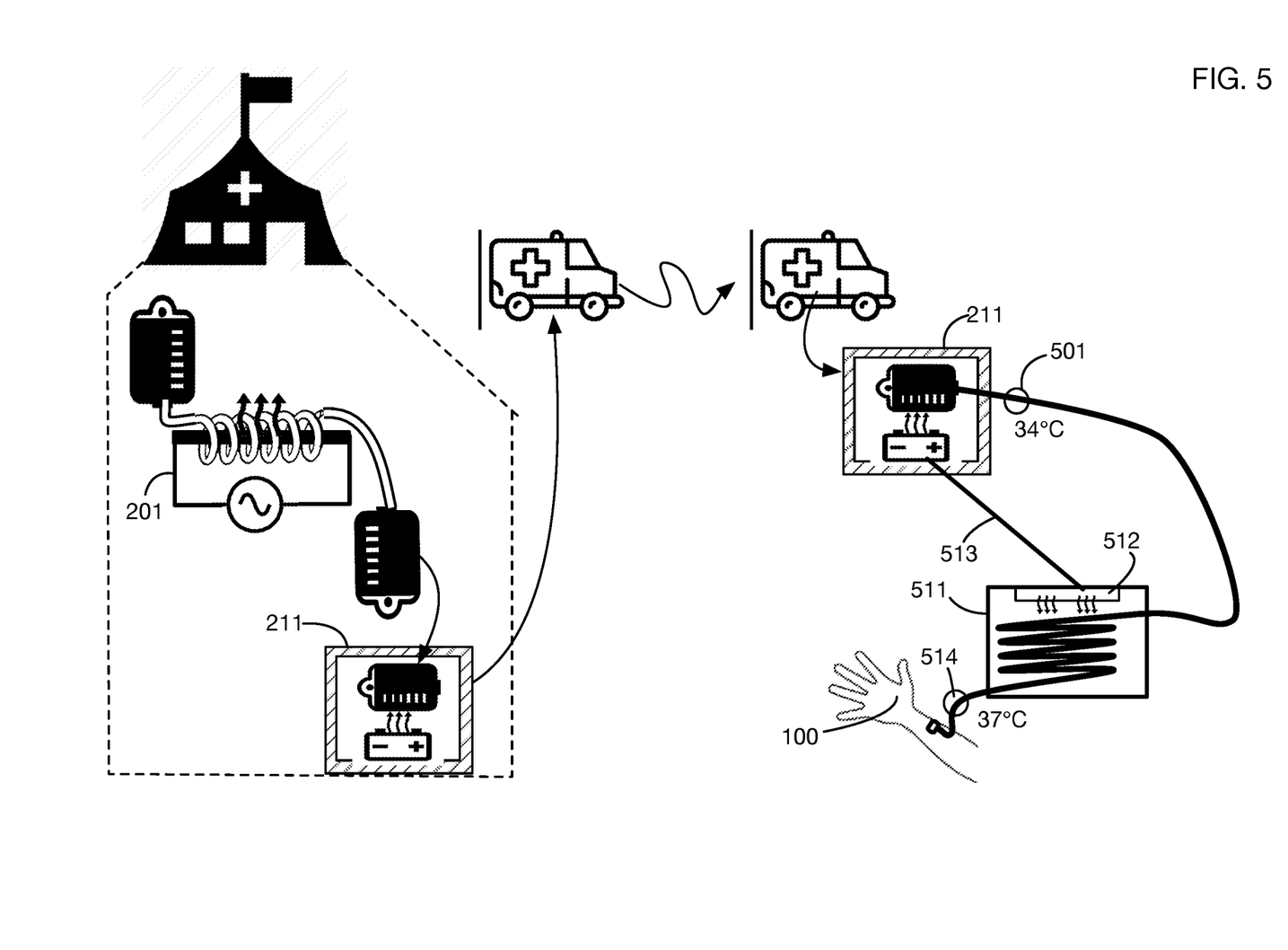
FIG. 5 shows an additional device that may be used in one or more embodiments of the invention: a transfusion temperature regulating device that makes final temperature adjustments on blood as it is transfused into a patient.

In many situations the two-stage system illustrated in FIG. 2, which includes rapid blood heating device 201 and portable heated blood transport device 211, provides a complete solution to delivery of heated blood to a patient in the field. In some scenarios, it may be desirable to add an additional component to the system that performs a third stage of final temperature regulation of blood as it is transfused into the patient. This situation may arise for example if there is a long delay in transport so that the temperature of blood in the transport device cannot be maintained precisely at the desired temperature throughout transport. It may also be desirable in some situations to perform a final temperature regulation to compensate for factors such as uneven heating of blood bags within the transport device or drops in temperature as blood flows from the transport device through tubing towards the patient. FIG. 5 shows an extension to the system of FIG. 2 that may be used in one or more embodiments of the invention. In this system, an additional transfusion temperature regulating device 511 is placed between the transport device 211 and the patient 100. As an illustration, this device may boost the temperature of blood from an outgoing temperature 501 from the transport device 211 to a desired temperature 514 as the blood enters the patient. In one or more embodiments the regulating device 511 may have a heating element 512 that is powered from a connection to the battery of transport device 513, which may make the regulating device 511 very lightweight. In one or more embodiments the regulating device 511 may have its own power supply instead of or in addition to using the power supply of the transport device 211.

Figure 6:
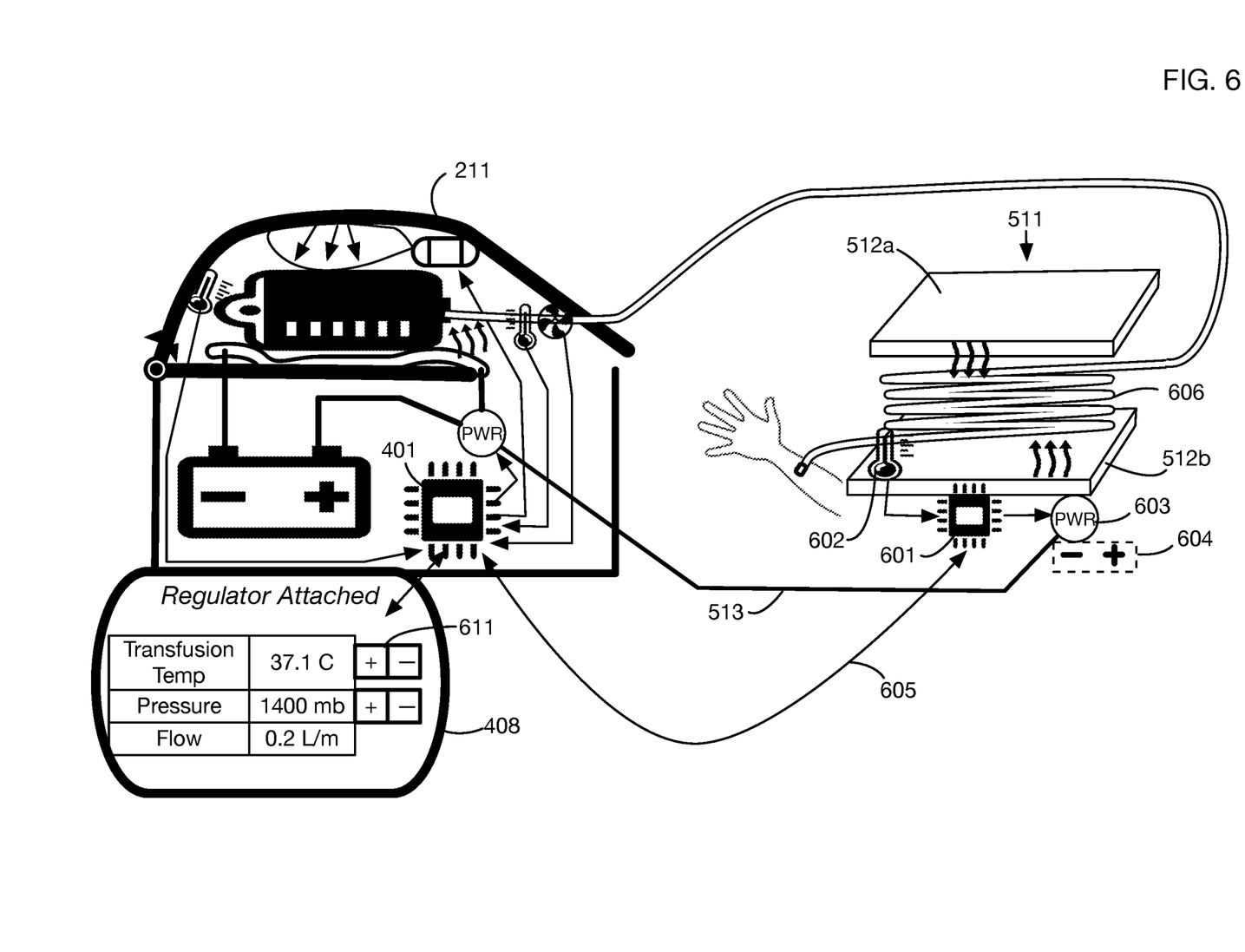
FIG. 6 shows illustrative components of an embodiment of the transfusion temperature regulating device.

FIG. 6 shows illustrative components of an embodiment of a transfusion temperature regulating device 511. Tubing 606 running from the output of transport device 211 may be placed into grooves or other features in the regulating device 511, for example in a serpentine pattern that increases the surface area of the tubing within the regulating device. In this illustrative embodiment, the tubing 606 is sandwiched between a top heating element 512a and a bottom heating element 512b; these two elements may hinge open so that tubing can be placed between them, for example. Like transport device 211, the transfusion temperature regulating device 511 may have a controller 601 that controls a power modulating element 603 that modifies the heat output of the heating elements to achieve a desired output temperature, as measured by an output temperature sensor 602. Regulating device controller 601 may be for example, without limitation, a microprocessor, a microcontroller, a processor, a CPU, a GPU, an ASIC, or a network connection to any other processor or processors. The power input to the power modulating element 603 may be a power line 513 from the transport device power supply, or it may include or consist of a separate battery or other contained power source 604.

In one or more embodiments the controller 601 of the transfusion temperature regulating device 511 may communicate with the controller 401 of the portable heated transport device 211 to optimize the heating of blood during a transfusion. These controllers may communicate over any link 605, which may be a wired or wireless network connection. For example, in one or more embodiments each of the devices 211 and 511 may include Bluetooth network interfaces for wireless communication between them. As the transfusion temperature regulating device 511 senses the output temperature of sensor 602, it may for example transmit a message to controller 401 to boost (or reduce) heating within the transport device 211, so that the heating elements 512a and 512b can maintain the final transfusion temperature within a desired range. The user interface 408 of the transport device 211 may also be used to control functions of the transfusion temperature regulating device; for example, in the scenario shown in FIG. 6 the user interface indicates that the regulator 511 is attached and the temperature controls 611 control the final output temperature measured by sensor 602.

While the invention herein disclosed has been described by means of specific embodiments and applications thereof, numerous modifications and variations could be made thereto by those skilled in the art without departing from the scope of the invention set forth in the claims.

What is claimed is:

1. A multi-stage blood warming system that enables field delivery of heated blood, comprising:
a rapid blood heating device comprising
an input line configured to be coupled to a supply of unheated blood;
a line coil coupled to the input line;
a heating device heating element proximal to the line coil and configured to heat blood passing through the line coil, wherein the heating device heating element is configured to be coupled electrically to a high-energy power source;
a heating device output line coupled to the line coil and configured to be connected to a blood bag and to supply heated blood into the blood bag;
a heating device output temperature sensor coupled to the heating device output line and configured to measure a temperature of blood passing through the heating device output line; and
a heating device controller coupled to the heating device output temperature sensor and to the heating device heating element and configured to adjust a heat output of the heating device heating element to maintain a temperature measured by the heating device output temperature sensor within a desired heating device temperature range; and,
a portable heated blood transport device comprising
a case configured to open and close;
an insulated cavity in the case configured to receive one or more blood bags filled with heated blood;
a battery contained within the case;
a transport device heating element coupled to the battery and located proximal to the one or more blood bags;
a transport device storage temperature sensor located proximal to the one or more blood bags; and
a transport device controller coupled to the transport device heating element and to the transport device storage temperature sensor and configured to adjust a heat output of the transport device heating element to maintain a temperature measured by the transport device storage temperature sensor within a desired transport device temperature range.

2. The multi-stage blood warming system of claim 1 wherein
the high-energy power source comprises an alternating current power source.

3. The multi-stage blood warming system of claim 1 wherein
the heating device heating element comprises an infrared lamp.

4. The multi-stage blood warming system of claim 3 wherein
the rapid blood heating device further comprises a reflective material surrounding the line coil,
wherein the reflective material reflects wavelengths emitted by the infrared lamp.

5. The multi-stage blood warming system of claim 4 wherein
the reflective material comprises aluminum.

6. The multi-stage blood warming system of claim 1 wherein
the rapid blood heating device further comprises a heating device input temperature sensor coupled to the input line and configured to measure a temperature of blood passing through the input line.

7. The multi-stage blood warming system of claim 1 wherein
the rapid blood heating device further comprises a bubble sensor configured to detect bubbles in blood passing through the heating device output line.

8. The multi-stage blood warming system of claim 1 wherein
the rapid blood heating device further comprises a heating device flow rate sensor configured to measure a flow rate of blood through the rapid blood heating device.

9. The multi-stage blood warming system of claim 1 wherein
the portable heated blood transport device further comprises
a transport device output line;
an inflatable bladder in the case that is in contact with the one or more blood bags; and
an air source coupled to the inflatable bladder and to the transport device controller;
the transport device controller is configured to inflate the inflatable bladder when the transport device controller receives a command to initiate a transfusion.

10. The multi-stage blood warming system of claim 9 wherein
the transport device controller is further configured to periodically inflate the inflatable bladder to mix blood within the one or more blood bags during transport.

11. The multi-stage blood warming system of claim 9 wherein
the portable heated blood transport device further comprises a pressure sensor configured to measure a pressure of air in the inflatable bladder.

12. The multi-stage blood warming system of claim 9 wherein
the portable heated blood transport device further comprises a transport device output temperature sensor coupled to the transport device output line.

13. The multi-stage blood warming system of claim 1 further comprising:
a transfusion temperature regulating device comprising
a regulating device input line configured to receive blood from one or more blood bags in the portable heated blood transport device;
a power line configured to be electrically coupled to the battery of the portable heated blood transport device;
a line heating path coupled to the regulating device input line;
a regulating device heating element that is
coupled to the power line;
proximal to the line heating path; and
configured to heat blood passing through the line heating path;
a regulating device output line coupled to the line heating path and configured to be coupled to a transfusion line into a patient;
a regulating device output temperature sensor coupled to the regulating device output line;
a regulating device controller coupled to the regulating device output temperature sensor and to the regulating device heating element and configured to adjust a heat output of the regulating device heating element to maintain a temperature measured by the regulating device output temperature sensor within a desired regulating device temperature range; and,
a communications interface configured to communicate with the transport device controller.

14. The multi-stage blood warming system of claim 13 wherein the regulating device controller is further configured to transmit a command to the transport device controller to modify the heat output of the transport device heating element based on the temperature measured by the regulating device output temperature sensor.

15. A multi-stage blood warming system that enables field delivery of heated blood, comprising:
a rapid blood heating device comprising
an input line configured to be coupled to a supply of unheated blood;
a line coil coupled to the input line;
a heating device heating element comprising an infrared lamp proximal to the line coil and configured to heat blood passing through the line coil, wherein the heating device heating element is configured to be coupled electrically to a high-energy power source comprising an alternating current power source;
a heating device output line coupled to the line coil and configured to be connected to a blood bag and to supply heated blood into the blood bag;
a reflective material comprising aluminum surrounding the line coil, wherein the reflective material reflects wavelengths emitted by the infrared lamp;
a heating device output temperature sensor coupled to the heating device output line and configured to measure a temperature of blood passing through the heating device output line;
a heating device input temperature sensor coupled to the input line and configured to measure a temperature of blood passing through the input line;
a bubble sensor configured to detect bubbles in blood passing through the heating device output line;
a heating device flow rate sensor configured to measure a flow rate of blood through the rapid blood heating device;
a heating device controller coupled to the heating device input temperature sensor, to the heating device output temperature sensor, to the bubble sensor, to the heating device flow rate sensor, and to the heating device heating element and configured to adjust a heat output of the heating device heating element to maintain a temperature measured by the heating device output temperature sensor within a desired heating device temperature range;
a portable heated blood transport device comprising
a case configured to open and close;
an insulated cavity in the case configured to receive one or more blood bags filled with heated blood;
a battery contained within the case;
a transport device heating element coupled to the battery and located proximal to the one or more blood bags;
a transport device storage temperature sensor located proximal to the one or more blood bags;
a transport device output line;
a transport device output temperature sensor coupled to the transport device output line;
an inflatable bladder in the case that is in contact with the one or more blood bags;
an air source coupled to the inflatable bladder;
a pressure sensor configured to measure a pressure of air in the inflatable bladder;
a transport device controller coupled to the transport device heating element, to the transport device storage temperature sensor, to the pressure sensor, to the transport device output temperature sensor, and to the air source, and configured to
adjust a heat output of the transport device heating element to maintain a temperature measured by the transport device storage temperature sensor within a desired transport device temperature range; and
inflate the inflatable bladder when the transport device controller receives a command to initiate a transfusion; and
periodically inflate the inflatable bladder to mix blood within the one or more blood bags during transport;
a transfusion temperature regulating device comprising
a regulating device input line configured to receive blood from one or more blood bags in the portable heated blood transport device;
a power line configured to be electrically coupled to the battery of the portable heated blood transport device;
a line heating path coupled to the regulating device input line;
a regulating device heating element that is
coupled to the power line;
proximal to the line heating path; and
configured to heat blood passing through the line heating path;
a regulating device output line coupled to the line heating path and configured to be coupled to a transfusion line into a patient;
a regulating device output temperature sensor coupled to the regulating device output line;
a regulating device controller coupled to the regulating device output temperature sensor and to the regulating device heating element and configured to adjust a heat output of the regulating device heating element to maintain a temperature measured by the regulating device output temperature sensor within a desired regulating device temperature range; and,
a communications interface configured to communicate with the transport device controller;
wherein the regulating device controller is further configured to transmit a command to the transport device controller to modify the heat output of the transport device heating element based on the temperature measured by the regulating device output temperature sensor.

* * * * *